United States Patent
Lörsch

(10) Patent No.: US 10,717,691 B2
(45) Date of Patent: Jul. 21, 2020

(54) PROCESS FOR THE PRODUCTION OF SEMIFLUORINATED ALKANES

(71) Applicant: NOVALIQ GMBH, Heidelberg (DE)

(72) Inventor: Lorenz Lörsch, Ladenburg (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 16/611,080

(22) PCT Filed: May 4, 2018

(86) PCT No.: PCT/EP2018/061473
§ 371 (c)(1),
(2) Date: Nov. 5, 2019

(87) PCT Pub. No.: WO2018/202835
PCT Pub. Date: Nov. 8, 2018

(65) Prior Publication Data
US 2020/0140358 A1 May 7, 2020

(30) Foreign Application Priority Data

May 5, 2017 (EP) .................................. 17169732

(51) Int. Cl.
| | | |
|---|---|---|
| C07C 17/25 | (2006.01) | |
| B01J 23/75 | (2006.01) | |
| B01J 23/72 | (2006.01) | |
| C07C 17/357 | (2006.01) | |
| B01J 23/745 | (2006.01) | |
| C07C 19/08 | (2006.01) | |
| C07C 17/23 | (2006.01) | |
| B01J 23/76 | (2006.01) | |

(52) U.S. Cl.
CPC ............... *C07C 17/25* (2013.01); *B01J 23/72* (2013.01); *B01J 23/745* (2013.01); *B01J 23/75* (2013.01); *B01J 23/76* (2013.01); *C07C 17/23* (2013.01); *C07C 17/357* (2013.01); *C07C 19/08* (2013.01)

(58) Field of Classification Search
CPC ....... C07C 19/08; C07C 17/25; C07C 17/357; C07C 17/23; B01J 23/72; B01J 23/745; B01J 23/76; B01J 23/75
See application file for complete search history.

(56) References Cited

U.S. PATENT DOCUMENTS

| | | |
|---|---|---|
| 2,616,927 A | 11/1952 | Kauck et al. |
| 5,077,036 A | 12/1991 | Long |
| 5,518,731 A | 5/1996 | Meadows |
| 5,874,469 A | 2/1999 | Maniar et al. |
| 5,874,481 A | 2/1999 | Weers et al. |
| 6,113,919 A | 9/2000 | Reiss et al. |
| 6,211,248 B1 * | 4/2001 | Menz ................... A61K 9/0026 514/743 |
| 6,262,126 B1 | 7/2001 | Meinert |
| 6,372,243 B2 | 4/2002 | Kobuch |
| 6,486,212 B2 | 11/2002 | Meinert |
| 8,614,178 B2 | 12/2013 | Theisinger et al. |
| 8,986,738 B2 | 3/2015 | Meinert |
| 9,241,900 B2 | 1/2016 | Wilson |
| 9,308,262 B2 | 4/2016 | Günther et al. |
| 9,757,459 B2 | 9/2017 | Günther et al. |
| 9,757,460 B2 | 9/2017 | Günther et al. |
| 9,770,508 B2 | 9/2017 | Günther et al. |
| 10,045,996 B2 | 8/2018 | Theisinger et al. |
| 2002/0128527 A1 | 9/2002 | Meinert |
| 2008/0234389 A1 | 9/2008 | Mecozzi et al. |
| 2010/0008996 A1 | 1/2010 | Meinert |
| 2013/0266652 A1 | 10/2013 | Theisinger et al. |
| 2014/0004197 A1 | 1/2014 | Theisinger et al. |
| 2015/0126785 A1 | 5/2015 | Sharratt et al. |
| 2015/0224064 A1 | 8/2015 | Gunther et al. |
| 2015/0238605 A1 | 8/2015 | Gunther et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2019/0070125 A1 | 3/2019 | Scherer et al. |

FOREIGN PATENT DOCUMENTS

| | | |
|---|---|---|
| WO | WO 93/16974 | 9/1993 |
| WO | WO 97/12852 | 4/1997 |
| WO | WO 97/12858 | 4/1997 |
| WO | WO 00/10531 | 3/2000 |
| WO | WO 2014/154531 | 10/2014 |
| WO | WO 2018/202835 | 11/2018 |

OTHER PUBLICATIONS

Barata-Vallejo et al., "(Me3Si)3 SiH-Mediated Intermolecular Radical Perfluoroalkylation Reactions of Olefins in Water," J. Org. Chem., 2010, 75:6141-6148.
Bardin et al., "Long-Range Nanometer-Scale Organization of Semifluorinated Alkane Monolayers at the Air/Water Interface," Langmuir, 2011, 27, 13497-13505.
Broniatowski, M. et al., "Langmuir Monolayers Characteristic of (Perfluorodecyl)-Alkanes," Journal of Physical Chemistry B, 2004, 108, 13403-13411.
Costa Gomes et al., "Solubility of dioxygen in seven fluorinated liquids," Journal of Fluorine Chemistry, 2004, 125, 1325-1329.
Davis et al., "Titanium-catalyzed addition of perfluoroalkyl iodides to alkenes," Journal of Fluorine Chemistry, 1995, 70(1): 135-140.
Dias et al., "Solubility of oxygen in liquid perfluorocarbons," Fluid Phase Equilibria, 2004, 222-223:325-330.
Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).
Hata, K. et al., "The Urushibara Hydrogenation Catalysts, A Review," Organic Preparations and Procedures International: The New Journal for Organic Synth, Organic Preparation and Procedures Co., 1972, 4(4): 179-209.
Holm, R. et al., "A novel excipient, 1-perfluorohexyloctane shows limited utility for the oral delivery of poorly water-soluble drugs," European Journal of Pharmaceutical Sciences, 2011, 42: 416-422.

(Continued)

*Primary Examiner* — Jafar F Parsa
(74) *Attorney, Agent, or Firm* — Hoxie & Associates LLC

(57) ABSTRACT

The present invention relates to a process for the production of semifluorinated alkanes.

26 Claims, 3 Drawing Sheets

(56) References Cited

OTHER PUBLICATIONS

International Preliminary Report on Patentability dated Nov. 5, 2019, for International Application No. PCT/EP2018/061473, 7 pages.
International Search Report for International Application No. PCT/EP2018/061473 dated Jun. 1, 2018, 4 pages.
Lo Nostro, P. et al., "Aggregation of a Semifluorinated n-Alkane in Perfluorooctane," J. Phys. Chem. 1993, 97:6535-6540.
Meinert, H. et al., "The Use of Semifluorinated Alkanes in Blood-Substitutes," Biomaterials, Artificial Cells, and Immobilization Biotechnology, 1993, 21 (5), 583-595.
Meinert, H. et al., "Semifluorinated Alkanes—A New Class of Compounds with Outstanding Properties for Use in Ophthalmology," European Journal of Ophthalmology, 2000, 10 (3), 189-197.
Richardson et al., "A convenient and practical method for the selective preparation of deuterofluorocarbons," Journal of Fluorine Chemistry, 2015, 180:208-215.
Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.
Tarrant et al., "Free Radical Additions Involving Fluorine Compounds. IV. The Addition of Dibromodifluoromethane to Some Fluoroölefins," Journal of the American Chemical Society, 1955, vol. 19: 2783-2787.
Von Werner et al., "13C-NMR Studies of Polyfluorinated Hydrocarbons, Carboxylic Acid Derivatives, Alcohols and Ethers," Journal of Fluorine Chemistry, 1982, 19:163-180.
Wong, D. et al., "Perfluorocarbon and Semifluorinated Alkanes," Seminars in Ophthalmology, 2000, 15 (1), 25-35.

\* cited by examiner

PROCESS FOR THE PRODUCTION OF SEMIFLUORINATED ALKANES

CROSS-REFERENCE TO RELATED APPLICATIONS

This application is a U.S. national stage application filed under 35 U.S.C. § 371 of International Application No. PCT/EP2018/061473, filed on May 4, 2018, which claims priority to, and the benefit of, European Application No. 17169732.9, filed on May 5, 2017, the contents of each of which are incorporated herein by reference in their entireties.

FIELD OF THE INVENTION

The present invention relates to a process for the production of semifluorinated alkanes.

BACKGROUND OF THE INVENTION

Semifluorinated alkanes are physically, chemically and physiologically inert compounds, which find application in medicine, in particular in the ophthalmic and dermatological field.

As described in Chem. Rev. 2009, 109, 1714-1792, a process commonly used for the production of semifluorinated alkanes is a process comprising the free radical addition of F-alkyl iodides, $C_nF_{2n+1}I$, to a multiple bond, followed by reductive dehalogenation of the resulting iodinated adduct. The addition of $C_nF_{2n+1}I$ onto a terminal alkene is commonly conducted in the presence of an azonitrile type radical generating chain initiator (e.g. 2,2'-azobis (isobutyronitrile), AIBN) according to the following scheme:

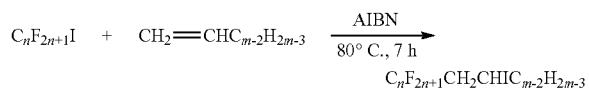

Reductive dehalogenation of the iodo-diblock intermediate $C_nF_{2n+1}CH_2CHIC_{m-2}H_{2m-3}$ is commonly performed with zinc powder and gaseous HCl in ethanol or another alcohol, acetic acid or aqueous HCl. In alternative processes, tributyltin hydride and LiAlH$_4$/ether are also used. Unsaturated diblocks can be converted to saturated ones using standard catalytic (rhodium or palladium on charcoal) hydrogenation procedures under pressure. Thorough purification of the diblock compounds is indispensable, especially when physicochemical investigation or biomedical applications are intended. It is usually achieved by distillation or recrystallization, sometimes followed by sublimation or passage over an alumina column. Filtration over activated alumina is strongly recommended when elimination of traces of potentially toxic material is essential.

Similar to the linear semifluorinated alkanes, the synthesis of semifluorinated alkanes with branched hydrocarbon chains comprises the free radical addition of F-alkyl iodides $C_nF_{2n+1}$ to a multiple bond, followed by reductive dehalogenation of the resulting iodinated adduct. An example of reductive dehalogenation of a iodinated compound with branched hydrocarbon chain has been reported as follows:

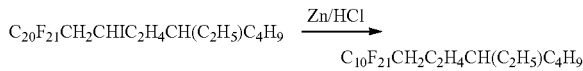

EP 0877 010 B1 describes inter alia the synthesis of 1-perfluorbutyl-3-methyl-butane in which reductive dehalogenation is performed with Zn/HCl.

The process comprising reductive dehalogenation by using Zn/HCl results in low yield and low purity, due to the presence of unsaturated species in the final product.

As another process for the production of semifluorinated alkanes, a process comprising reductive dehalogenation of the iodinated adduct by using Pd/C and H$_2$ has been reported, see WO 97/12852. This process however requires the use of pressure reactors, long reaction time and results not to be economical.

SUMMARY OF THE INVENTION

Problem to be Solved by the Invention

It is an object of the present invention to provide a novel method for producing semifluorinated alkanes which is industrially efficient and convenient in terms of costs, reaction time, yield of the final product and ease of operation.

Means to Solve the Problem

The present invention provides the following:
(1) A method for producing a semifluorinated alkane compound represented by the formula (1)

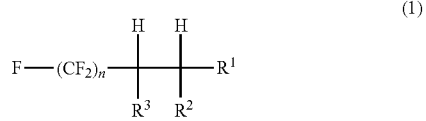

which comprises subjecting a compound of the formula (2)

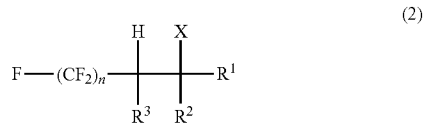

to reductive dehalogenation reaction in the presence of a Urushibara metal catalyst and a reducing agent,
wherein in the formula (1) and (2) n is an integer from 2 to 12;
$R^1$, $R^2$ and $R^3$ are the same or different and are independently from each other selected from hydrogen and a $C_{1-10}$ linear or branched alkyl group; and
X is a halogen atom selected from chlorine, bromine and iodine.
(2) The method according to (1), wherein $R^1$ is selected from hydrogen and a $C_{1-10}$ linear or branched alkyl group; $R^2$ and $R^3$ are independently from each other selected from hydrogen and a $C_{1-10}$ linear alkyl group.
(3) The method according to (2), wherein $R^1$ is selected from hydrogen and a $C_{1-10}$ linear or branched alkyl group; $R^2$ and $R^3$ are independently from each other selected from hydrogen and a $C_{1-6}$ linear alkyl group.

(4) The method according to (3), wherein $R^1$ is selected from hydrogen and a $C_{1-6}$ linear or branched alkyl group; $R^2$ and $R^3$ are independently from each other selected from hydrogen and a methyl group.
(5) The method according to (4), wherein $R^1$, $R^2$ and $R^3$ are hydrogen; or
wherein $R^1$ and $R^2$ are hydrogen; $R^3$ is methyl; or
wherein $R^1$ is methyl, $R^2$ is hydrogen and $R^3$ is methyl; or
$R^1$ and $R^2$ are methyl, $R^3$ is hydrogen; or
$R^1$ is ethyl, $R^2$ is methyl, $R^3$ is hydrogen; or
$R^1$ is isopropyl, $R^2$ and $R^3$ are hydrogen; or
$R^1$ is a $C_{1-6}$ linear alkyl group, $R^2$ and $R^3$ are hydrogen.
(6) The method according to (1), wherein $R^1$, $R^2$, $R^3$ are independently from each other one selected from hydrogen, methyl, ethyl, propyl, isopropyl, butyl, sec-butyl, isobutyl, tert-butyl, pentyl, isopentyl, neopentyl, hexyl.
(7) The method according to any of (1) to (6), wherein n is an integer selected from 4 to 10.
(8) The method according to (7), wherein n is an integer selected from 4 to 8.
(9) The method according to any of (1) to (8), wherein the Urushibara metal catalyst is selected from one prepared by using nickel, cobalt, iron or copper as a metal.
(10) The method according to (9), wherein the Urushibara metal catalyst is selected from one prepared by using iron or copper as a metal.
(11) The method according to any of (1) to (10), wherein the amount of Urushibara metal catalyst is from 8 to 12 weight percent (wt %) based on the amount of the compound of formula (2).
(12) The method according to any of (1) to (11), wherein the reducing agent is selected from a complex compound of borohydride and a complex compound of aluminium hydride.
(13) The method according to (12), wherein the reducing agent is selected from sodium borohydride, lithium borohydride, potassium borohydride, calcium borohydride, zinc borohydride, triacetoxy sodium borohydride, sodium cyano borohydride and lithium aluminium hydride.
(14) The method according to (13), wherein the reducing agent is sodium borohydride.
(15) The method according to any of (1) to (14), wherein the amount of the reducing agent is from 2 to 6 equivalents with regard to the compound of formula (2).
(16) The method according to any of (1) to (15), wherein the reductive dehalogenation is carried out by using as a solvent an alcohol selected from ethanol, methanol and iso-propanol or a mixture thereof.
(17) The method according to any of (1) to (16), wherein $R^1$ is selected from hydrogen and a linear $C_{1-6}$ alkyl group, $R^2$ and $R^3$ are hydrogen.
(18) The method according to any of (1) to (17), wherein X is a halogen atom selected from iodine.

The invention further relates to the use of an Urushibara metal catalyst in a method for the production of a semifluorinated alkane of Formula 1

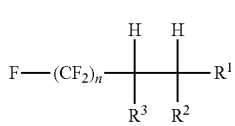

comprising the reductive dehalogenation of a compound of Formula 2

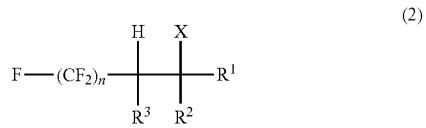

wherein the definitions of n, X, $R^1$, $R^2$ and $R^3$ are the same as given above.

Effect of the Invention

The process of the present invention for producing semifluorinated alkanes has the following characteristics: the method is simple in operation, selective, not expensive and is useful as industrial manufacturing process.

DETAILED DESCRIPTION OF THE INVENTION

Figure 1:
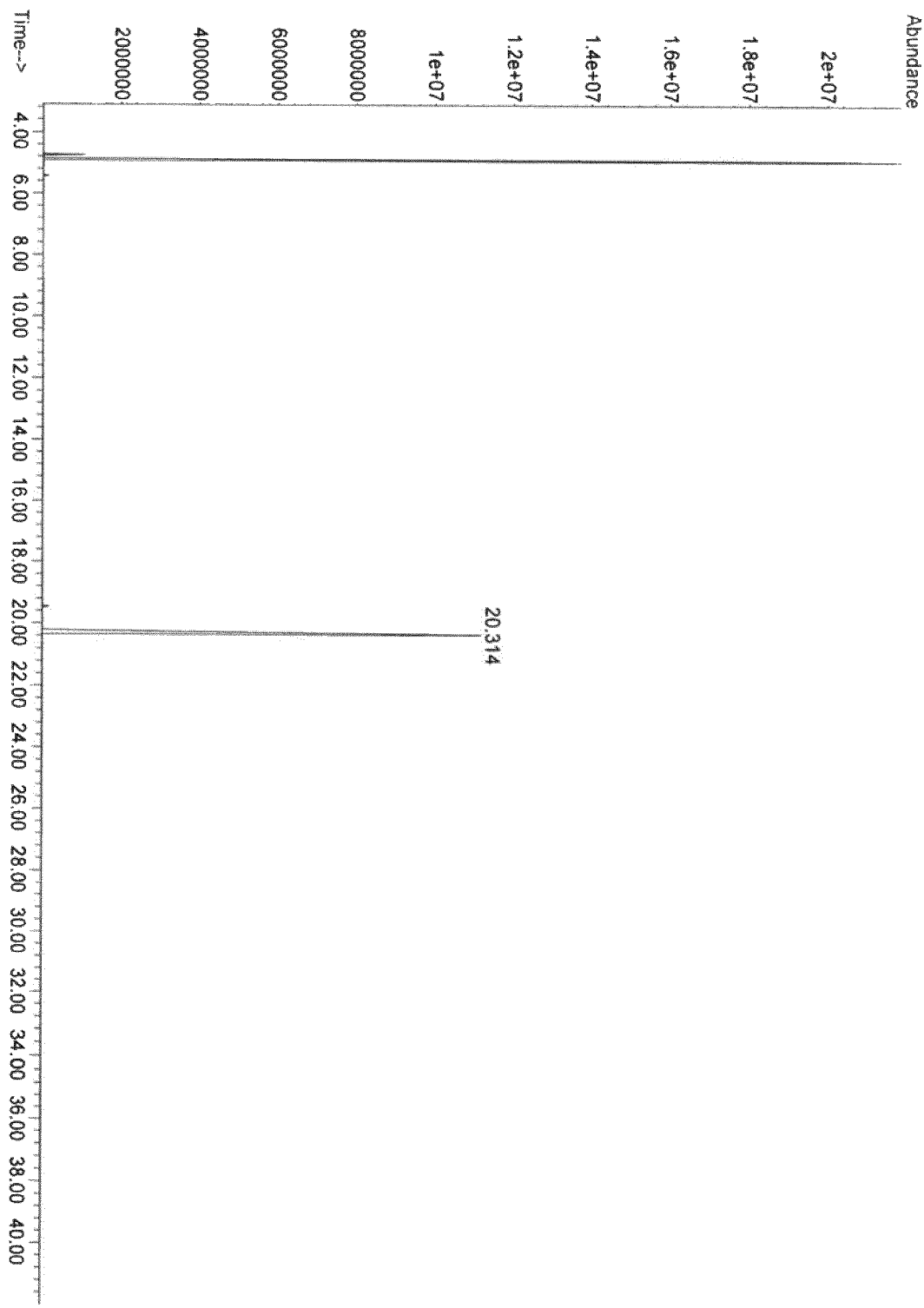
FIG. 1: GC/MS spectrum of F6H8

The present invention relates to a method for producing a semifluorinated alkane compound represented by the formula (1)

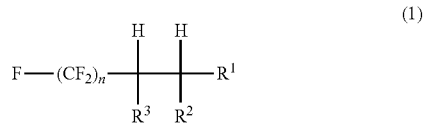

comprising subjecting a compound of the formula (2)

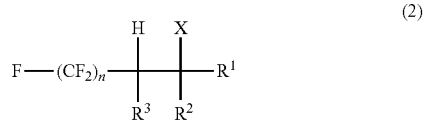

to reductive dehalogenation reaction in the presence of a Urushibara metal catalyst, and a reducing agent,
wherein in the formula (1) and (2)
n is an integer from 2 to 12;
$R^1$, $R^2$ and $R^3$ are the same or different and are independently from each other one selected from hydrogen and a $C_{1-10}$ linear or branched alkyl group;
X is a halogen atom selected from chlorine, bromine and iodine.

The term "semifluorinated alkane" (also referred to as "SFA") as used herein in reference to a compound of Formula (I) refers to a linear or branched compound composed of one perfluorinated segment (F-segment) and at least one non-fluorinated hydrocarbon segment (H-segment). Within the context of the present invention, the following nomenclature for a linear semifluorinated alkane FnHm may also be used, wherein F means the perfluorinated hydrocarbon segment, H means the non-fluorinated hydrocarbon segment and n, m is the number of carbon atoms of the respective segment. For example, F4H5 is used for 1-perfluorobutyl pentane.

Liquid SFA's are chemically and physiologically inert, colourless and stable. Their typical densities range from 1.1 to 1.7 g/cm$^3$, and their surface tension may be as low as 19 mN/m.

SFA's of the FnHm type are insoluble in water but also somewhat amphiphilic, with increasing lipophilicity correlating with an increasing size of the non-fluorinated segment.

Reductive dehalogenation generally refers to the reduction of an alkyl halide to the corresponding alkane. In the present invention, the reductive dehalogenation is the dehalogenation of a halogenated adduct of a semifluorinated alkane to the corresponding semifluorinated alkane.

The semifluorinated alkane product according to the invention is compound of Formula 1:

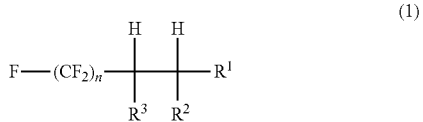

(1)

wherein n is an integer from 2 to 12; and
$R^1$, $R^2$ and $R^3$ are the same or different and are independently from each other selected from hydrogen and a $C_{1-10}$ linear or branched alkyl group.

The precursor for said semifluorinated alkane is of Formula 2:

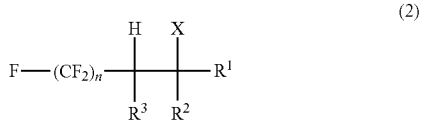

(2)

wherein n is an integer from 2 to 12;
$R^1$, $R^2$ and $R^3$ are the same or different and are independently from each other selected from hydrogen and a $C_{1-10}$ linear or branched alkyl group; and X is a halogen atom selected from chlorine, bromine and iodine.

This precursor also comprises a F-segment and a H-segment, as defined for the SFA of Formula (1). Unless indicated otherwise, all definitions and descriptions relating to semifluorinated alkanes as described herein, in particular semifluorinated alkane of Formula (1) are applicable to the precursor of Formula (2) as well.

Moreover, the method according to the invention is applicable, independent of the stereoconfiguration of the compound of formula (2).

Preferably, the method is used for the preparation of a semifluorinated alkane which is a compound that exists in a liquid state, at least at one temperature within the temperature range of 4° to 40° C.

In the formula (2), X is a halogen selected from chlorine, bromine and iodine. In a preferred embodiment of the present invention, X is selected from bromine and iodine. In a more preferred embodiment of the present invention, X is iodine.

In the above formulae (1) and (2), n is an integer of from 2 to 12. Preferably, n represents an integer of from 4 to 10. More preferably, n represents an integer of from 4 to 8.

$R^1$, $R^2$ and $R^3$ are the same or different. Independently from each other, $R^1$, $R^2$ and $R^3$ are selected from H (hydrogen) and a $C_{1-10}$ linear or branched alkyl group. For example, a $C_{1-10}$ linear alkyl group may be methyl, ethyl, propyl, butyl, pentyl, hexyl, heptyl, octyl, nonyl or decyl; a $C_{1-10}$ branched alkyl group may, for example, be isopropyl, sec-butyl, isobutyl, tert-butyl, isopentyl, or neopentyl.

Preferably, $R^1$ is selected from hydrogen, methyl, ethyl, propyl, isopropyl, butyl, sec-butyl, isobutyl, tert-butyl, pentyl, isopentyl, neopentyl, and hexyl. More preferably, $R^1$ is hydrogen, methyl, ethyl, propyl, isopropyl, butyl, pentyl, or hexyl. Even more preferably, $R^1$ is hydrogen or a $C_{1-6}$ linear alkyl group.

Preferably, $R^2$ is selected from hydrogen, methyl, ethyl, propyl, isopropyl, butyl, sec-butyl, isobutyl, tert-butyl, pentyl, isopentyl, neopentyl, hexyl. More preferably, $R^2$ is hydrogen or a $C_{1-6}$ linear alkyl group. Even more preferably, $R^2$ is hydrogen or a methyl group.

Preferably $R^3$ is selected from hydrogen, methyl, ethyl, propyl, isopropyl, butyl, sec-butyl, isobutyl, tert-butyl, pentyl, isopentyl, neopentyl, hexyl. More preferably, $R^3$ is hydrogen or a $C_{1-6}$ linear alkyl group. Even more preferably, $R^3$ is hydrogen or methyl.

In a preferred embodiment of the present invention, $R^1$ is selected from hydrogen and a $C_{1-6}$ linear or branched alkyl group, $R^2$ is selected from hydrogen and a $C_{1-6}$ linear or branched alkyl group; $R^3$ is a selected from hydrogen and a $C_{1-6}$ linear alkyl group.

In a further preferred embodiment of the present invention, $R^1$ is hydrogen or a $C_{1-6}$ linear or branched alkyl group, $R^2$ and $R^3$ are hydrogen.

In yet a further embodiment of the present invention, the method for producing a semifluorinated alkane compound represented by the formula (1)

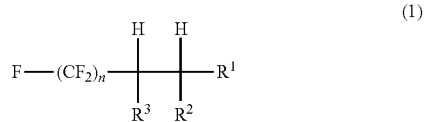

(1)

may comprise subjecting a compound of the formula (2)

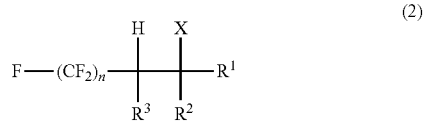

(2)

to reductive dehalogenation reaction in the presence of a Urushibara metal catalyst, and a reducing agent,
wherein in the formula (1) and (2):
n is an integer from 4 to 8;
X is iodine; and
$R^1$ is hydrogen, $R^2$ is hydrogen and $R^3$ is methyl; or
$R^1$ is methyl, $R^2$ is hydrogen and $R^3$ is methyl; or
$R^1$ is methyl, $R^2$ is methyl and $R^3$ is hydrogen; or
$R^1$ is ethyl, $R^2$ is methyl and $R^3$ is hydrogen; or
$R^1$ is iso-propyl, $R^2$ is hydrogen and $R^3$ is hydrogen; or
$R^1$ is a $C_{2-6}$ linear alkyl group, $R^2$ and $R^3$ are hydrogen.

In another further embodiment, the invention preferably relates to a method for preparing a semifluorinated alkane compound represented by the formula (1)

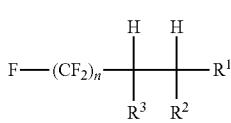

(1)

comprising subjecting a compound of the formula (2)

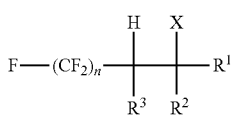

(2)

to reductive dehalogenation reaction in the presence of a Urushibara metal catalyst, and a reducing agent,
wherein in the formula (1) and (2):
n is 4, $R^1$ is n-propyl, $R_2$ is hydrogen and $R^3$ is hydrogen; or
n is 4, $R^1$ is n-butyl, $R_2$ is hydrogen and $R^3$ is hydrogen; or
n is 6, $R^1$ is n-butyl, $R_2$ is hydrogen and $R^3$ is hydrogen; or
n is 6, $R^1$ is n-hexyl, $R_2$ is hydrogen and $R^3$ is hydrogen; or
n is 8, $R^1$ is n-hexyl, $R_2$ is hydrogen and $R^3$ is hydrogen; and X is iodine.

The compounds of formula (1) and (2) may alternatively be expressed as linear chemical formulas.

The method is also applicable to any semifluorinated alkane with the general formula $C_nF_{2n+1}C_mH_{2m+1}$. Preferably, the semifluorinated alkane is an alkane as defined above. More preferably, the semifluorinated alkane is of formula $C_nF_{2n+1}C_mH_{2m+1}$, wherein n and m are integers independently selected from the range of 2 to 12, preferably selected from the range of 4 to 10, and even more preferably selected from the range of 4 to 8 carbon atoms.

Preferably the precursor of said SFA semifluorinated alkane is of the formula $C_nF_{2n+1}CH_2CHXC_{m-2}H_{2m-3}$, wherein n and m are integers independently selected from the range of 2 to 12, preferably selected from the range of 4 to 10, and even more preferably selected from the range of 4 to 8 carbon atoms. X is a halogen atom selected from chlorine, bromine, or iodine. Most preferably, X is iodine.

Accordingly, in a preferred embodiment the method of the invention may relate to the preparation of a semifluorinated alkane of the formula $F(CF_2)_n(CH_2)_mH$, wherein n and m are integers independently selected from the range of 2 to 12, preferably selected from the range of 4 to 10 and even more preferably selected from the range of 4 to 8 carbon atoms.

In a most preferred embodiment the precursor is a linear precursor of the formula $F(CF_2)_n(CH_2)(CHX)(CH_2)_{m-2}H$, wherein n and m are integers independently selected from the range of 2 to 12, preferably selected from the range of 4 to 10, and even more preferably selected from the range of 4 to 8 carbon atoms. X is a halogen atom selected from chlorine, bromine, or iodine. Most preferably, X is iodine. In preferred specific embodiments of the method of the invention, the semifluorinated alkane to be prepared is a linear semifluorinated alkane of the formula $F(CF_2)_n(CH_2)_mH$ selected from the group consisting of F4H5 ($F(CF_2)_4(CH_2)_5H$), F6H8 ($F(CF_2)_6(CH_2)_8H$), F8H8 ($F(CF_2)_8(CH_2)_8H$), F4H6 ($F(CF_2)_4(CH_2)_6H$) and F6H6 ($F(CF_2)_6(CH_2)_6H$).

In preferred specific embodiments, the precursor $F(CF_2)_nCH_2(CHX)(CH_2)_{m-2}H$ is selected from the group consisting of $F(CF_2)_4CH_2(CH1)(CH_2)_3H$, $F(CF_2)_6 CH_2(CH1)(CH_2)_6H$, $F(CF_2)_8CH_2(CH1)(CH_2)_6H$, $F(CF_2)_4 CH_2(CH1)(CH_2)_4H$ and $F(CF_2)_6CH_2(CH1)(CH_2)_4H$.

The reducing agent which is featured in the method of the present invention may be selected from a complex compound of borohydride, a complex compound of aluminium hydride. As a reducing agent in the method of the present invention, a compound represented by the following formula (3)

 (3)

may be used, wherein M represents an alkali metal atom such as lithium, sodium or potassium, and Z represents a hydrogen atom, a cyano group, an alkoxy group or an acyloxy group. As the alkoxy group, alkoxy groups having 1 to 6 carbon atoms are preferable. Examples of the acyloxy group include an alkylcarbonyloxy group, an arylcarbonyloxy group and an aralkylcarbonyloxy group. These alkoxy groups or acyloxy groups may be further substituted by a halogen atom. Specific examples of the alkoxy group or the acyloxy group include an acetyloxy group, a trifluoroacetyloxy group, a benzoyloxy group or a benzylcarbonyloxy group. In the formula (3), x is an integer of 1 to 4 and y is an integer of 0 to 3, and the sum of x and y is 4.

The compound of formula (3) may be generally selected from sodium borohydride, lithium borohydride, potassium borohydride, sodium cyano borohydride, sodium alkoxyborohydride and sodium acyloxy borohydride. As an alkoxy group of sodium alkoxyborohydride, alkoxy groups having 1 to 6 carbon atoms are preferable. In a preferred embodiment, lithium borohydride, sodium borohydride, sodium cyanoborohydride and triacetoxy sodium borohydride are preferred as reducing agent. In a more preferred embodiment of the invention, the reducing agent is sodium borohydride.

Preferably, a complex compound of borohydride such as sodium borohydride, lithium borohydride, potassium borohydride, calcium borohydride, zinc borohydride, triacetoxy sodium borohydride, sodium cyano borohydride or mixtures thereof, may be used as the reducing agent in the method according to the present invention.

Alternatively, the reducing agent used in the reaction and method according to the invention maybe a complex compound of aluminium hydride, such as lithium aluminium hydride.

In a preferred embodiment of the present invention, the reducing agent may be selected from sodium borohydride, lithium borohydride, potassium borohydride, calcium borohydride, zinc borohydride, triacetoxy sodium borohydride, sodium cyano borohydride and lithium aluminium hydride.

In a more preferred embodiment of the present invention, the reducing agent is selected from sodium borohydride, lithium borohydride, triacetoxy sodium borohydride and sodium cyano borohydride.

In a most preferred embodiment of the invention the reducing agent is sodium borohydride ($NaBH_4$). Sodium borohydride is a cheap metal hydride commercially available, is safe with regard to storage, use and handling.

The reducing agent can be used in an amount in the range of preferably from 1.0 to 10.0 equivalents, more preferably from 2 to 8 equivalents with regard to the compound of formula (2). As used herein, the term equivalent refers to molar equivalent.

In a preferred embodiment, the reducing agent is used in an amount in the range of from 2 to 6 equivalents with regard to the compound of formula (2), preferably from 3 to 5 equivalents with regard to the compound of formula (2). In a more preferred embodiment, the reducing agent is used in an amount of 4 equivalents with regard to the compound of formula (2).

The Urushibara metal catalyst may be a commercially available product or one prepared by a method as exemplified.

In a preferred embodiment, the Urushibara metal catalyst is freshly prepared. Methods of preparation for Urushibara metal catalysts are described in the art, see for example Taira, Shinichi (1961). Bulletin of the Chemical Society of Japan. 34 (2): 261-270.

As a general method for the preparation of an Urushibara metal catalyst, the following can be mentioned:

A metal is precipitated as a finely divided powder from an aqueous solution of its salt with another metal of a greater ionization tendency in powder or fine granular form. Then, the precipitated metal, not yet catalytically active, is digested with an aqueous solution of an alkali or acid. The starting salts are mostly chlorides and sometimes acetates. The precipitant metal is zinc dust or grained aluminium. In the present invention, the metal may be mixed in elemental form with zinc dust or grained aluminium. In the present invention, the Urushibara metal catalysts are preferably obtained by using zinc as precipitant metal. The digesting reagent may be chosen from among the following: caustic alkalis, ammonia, acetic acid, propionic acid and hydrochloric acid. Digestion with the basic or acidic reagent removes a basic salt of the precipitant metal covering the surface of the potential catalyst to expose the active surface.

However, sodium hydroxide and acetic acid are generally used. Preferably in the present invention the Urushibara metal catalysts are prepared via a method involving treatment with sodium hydroxide or acetic acid, more preferably with sodium hydroxide.

The Urushibara metal catalysts used in the context of the present method of the invention are preferably based on a metal selected from the group consisting of nickel (Ni), cobalt (Co), iron (Fe) and copper (Cu). More preferably, the Urushibara catalyst used in the context of the present invention is based on iron or copper as the metal. Most preferably, the Urushibara catalyst is based on iron as a metal, i.e. an Urushibara iron catalyst is preferably used in the method of preparing any one of the above described semifluorinated alkanes.

Acronyms may be used to designate the method of preparation of Urushibara metal catalysts. For example, the acronym U-X-A implies digestion with an acid, while U-X-B implies digestion with a base, wherein X represents the metal atom. In the present invention, the Urushibara catalysts are preferably digested with a base, that is they are preferably of the U-X-B type.

In a preferred embodiment of the present invention, the Urushibara metal catalyst is one selected from U—Ni—B, U—Co—B, U—Fe—B and U—Cu—B. In a more preferred embodiment of the present invention, the Urushibara catalyst is selected from U—Fe—B and U—Cu—B. In a most preferred embodiment of the present invention, the Urushibara catalyst is U—Fe—B.

In particular, the Urushibara metal catalysts are preferably prepared by using a metal selected from the group consisting of nickel (Ni), cobalt (Co), iron (Fe) and copper (Cu). More preferably, the Urushibara metal catalyst is one prepared by using iron or copper as a metal. Most preferably, the Urushibara metal catalyst is one prepared by using iron as a metal.

In a preferred embodiment, the Urushibara metal catalyst is a Urushibara metal catalyst obtainable, or prepared by the following method:

a) providing a metal selected from iron, nickel, cobalt or copper, preferably in powdered form or as a salt of the metal;
b) mixing said metal with a precipitant metal, preferably selected from aluminium or zinc, wherein the said precipitant metal is provided in powdered or grained form and in excess;
c) digesting or washing the composition with an acidic or basic reagent.

Preferably, said metal in step a) is copper, iron or cobalt. More preferably, said metal in step a) is iron or copper. Most preferably, said metal in step a) is iron.

In a preferred embodiment, said precipitant metal is zinc. The digestion is preferably performed with acetic acid or sodium hydroxide. Most preferably, the digestion is performed with sodium hydroxide.

In a preferred embodiment, the Urushibara metal catalyst is an Urushibara iron catalyst obtainable, or prepared by the following method:

a) combining elemental iron in powdered form with an excess of zinc or aluminium in powdered or grained form;
b) digesting or washing the composition with a basic reagent.

In a preferred embodiment, iron is combined with an excess of zinc. Preferably, the digestion is performed with sodium hydroxide.

In an alternative embodiment, the Urushibara metal catalyst is a Urushibara metal catalyst obtainable, or prepared by the following method steps:

a) providing a metal salt;
b) dissolving the metal salt;
c) adding a precipitant metal to the composition to allow the metal from the metal salt to precipitate, wherein the said precipitant metal is provided in excess;
d) digesting the composition with an acidic or basic reagent.

Preferably, said metal salt is a chloride, acetate or carbonate, preferably nickel chloride, iron chloride, cobalt chloride or copper chloride. More preferably, said salt is nickel chloride or iron chloride. Most preferably, said metal chloride salt is iron chloride.

In an alternative embodiment, said metal salt is an acetate, for example iron acetate. Preferably, the metal salt is provided and dissolved in an aqueous solution prior to addition with a precipitant metal.

In a preferred embodiment, said precipitant metal is aluminium, or zinc, preferably provided in a powder or grained form. In a more preferred embodiment, said precipitant metal is zinc.

The digestion is preferably performed with acetic acid or sodium hydroxide. Most preferably, the digestion is performed with sodium hydroxide.

In a further embodiment, the Urushibara metal catalyst is a Urushibara metal catalyst may be prepared by the following method:

a) providing a metal chloride salt;
b) dissolving the metal chloride salt;
c) adding a precipitant metal to the composition to allow the metal from the metal chloride to precipitate, wherein the said precipitant metal is provided in excess;
d) digesting the composition with an acidic or basic reagent.

Preferably, said metal chloride salt is nickel chloride, iron chloride, cobalt chloride or copper chloride. More preferably, said metal chloride salt is iron chloride. In another preferred, embodiment, said metal salt is an acetate, for example iron acetate. Preferably, the metal salt is provided and dissolved in an aqueous solution prior to addition of the precipitant metal. In a preferred embodiment said precipitant metal is zinc, preferably in a powder or fine granular form. The digestion is preferably performed with acetic acid or sodium hydroxy. Most preferably, the digestion is performed with sodium hydroxide.

The amount of the Urushibara metal catalyst is preferably from 1 wt % to 20 wt % based on the amount of the compound of formula (2). In a preferred embodiment of the present invention, the amount of catalyst is from 6 wt % to 14 wt % based on the amount of the compound of formula (2). In a more preferred embodiment, the amount of catalyst is from 8 to 12 wt % based on the amount of the compound of formula (2). In a most preferred embodiment, the amount of catalyst is from 9 to 11 wt % based on the amount of the compound of formula (2).

The solvent for the reductive dehalogenation reaction according to the invention is not particularly limited as long as it is stable under the reaction conditions. Solvents which may be used include, for example, protic solvents. A protic solvent is a solvent that has a hydrogen atom bound to an oxygen (as in a hydroxyl group) or a nitrogen (as in an amine group). In general terms, any solvent that contains labile H+ is called a protic solvent. These solvents may suitably be selected for use depending upon efficiency of the reaction therein, and may be used alone, respectively, or in combination as a mixture of two or more of them. In the present invention, the solvent is preferably a linear or branched $C_{1-10}$ alcohol. In a preferred embodiment, the solvent is one selected from methanol, ethanol, propan-2-ol, propan-1-ol, butan-1-ol, butan-2-ol, 2-methyl-1-propanol, 2-methyl-2-propanol, pentan-1-ol, 3-methyl-1-butanol, pentan-2-ol, 2-methyl-2-butanol, hexan-1-ol and mixtures thereof. In a more preferred embodiment of the present invention, the solvent is selected from methanol, ethanol, 2-propanol and mixtures thereof. In a most preferred embodiment of the present invention, the solvent is ethanol, methanol or a mixture thereof. Most preferably, the solvent is ethanol.

The amount of solvent used is not particularly limited, but preferably is 1 to 50 times volume per weight (v/w) of the compound of formula (2). In a preferred embodiment of the present invention, the amount of solvent is 1 to 20 v/w, volume per weight of the compound of formula (2). In a more preferred embodiment, the amount of solvent is 3 to 15 v/w of the compound of formula (2). In a most preferred embodiment, the amount of solvent is 3 to 8 v/w of the compound of formula (2).

In the process according to the present invention, the compound of formula (1) may be produced by reaction with a reducing agent in the presence of a Urushibara metal catalyst for 1 to 24 hours.

In a preferred embodiment of the present invention, the reaction may be completed in 2 to 8 hours, preferably in 2 to 6 hours, more preferably in 3 to 5 hours. In a more preferred embodiment the reaction is completed in 4 hours. As understood herein, reaction completion may be understood as the completed consumption of a compound of Formula (2) i.e. termination of conversion of Formula (2) to Formula (1), such as determined or monitored by GC-MS or $^1$HNMR analysis or other analytical methods in the art.

The reaction temperature is not particularly limited, but it is preferably in the range of 5° C. up to the boiling point of the solvent. The boiling point of some alcohols which can be used in the present invention are herewith given: methanol 65° C., ethanol 78° C., 2-propanol 82° C., tert-butyl alcohol 83° C., tert-amyl alcohol 102° C., n-propyl alcohol 97° C., 2-butanol 97° C., 2-methyl-1-propanol 108° C., 1-butanol 118° C., 1-pentanol 137° C. Preferably the method of the present invention is carried out under reflux conditions.

After completion of the reaction, the compound of formula (1) is collected from the reaction mixture according to a method usually employed. For example, the compound of formula (1) can be collected by removing inorganic substances as an aqueous layer and distilling off the solvent in the organic layer. The obtained target compound can be further purified by distillation or chromatography according to need.

In a preferred embodiment of the invention, the method for preparing a semifluorinated alkane compound represented by the formula (1)

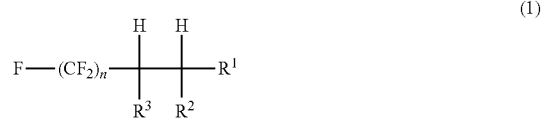

comprises subjecting a compound of the formula (2)

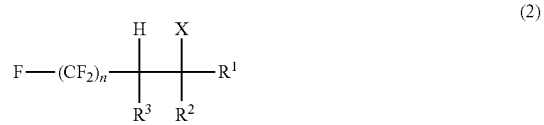

to reductive dehalogenation reaction in the presence of 6 wt % to 14 wt % based on the amount of the compound of formula (2) of an Urushibara metal catalyst, 2 to 6 molar equivalents of a reducing agent selected from a compound of formula $MBH_xZ_y$, wherein M represents an alkali metal atom selected from lithium, sodium and potassium, and Z represents a hydrogen atom, a cyano group, an alkoxy group or an acyloxy group, and x is an integer of 1 to 4 and y is an integer of 0 to 3, and the sum of x and y is 4;

wherein in the formula (1) and (2)

n is an integer from 2 to 12;

$R^1$, $R^2$ and $R^3$ are the same or different and are independently from each other one selected from hydrogen and a $C_{1-10}$ linear or branched alkyl group;

X is a halogen atom selected from chlorine, bromine and iodine; and optionally, wherein the reductive dehalogenation reaction is conducted in a linear or branched $C_{1-10}$ alcohol as a solvent.

In further embodiment of the invention, the method for producing a semifluorinated alkane compound represented by the formula (1)

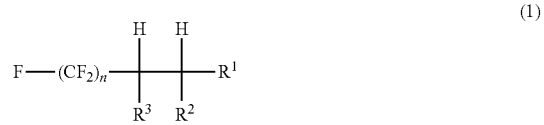

comprises subjecting a compound of the formula (2)

to reductive dehalogenation reaction in the presence of 9 wt % to 11 wt % of an Urushibara metal catalyst based on the amount of compound of formula (2), wherein the Urushibara metal catalyst is prepared from iron or copper; 3 to 5 molar equivalents of a reducing agent selected from sodium borohydride ($NaBH_4$),
wherein in the formula (1) and (2)
n is an integer from 4 to 8;
$R^1$ is a $C_{1-10}$ linear alkyl or branched group, preferably selected from ethyl, n-propyl, n-butyl, n-pentyl and n-hexyl;
$R^2$ and $R^3$ are both selected from hydrogen;
X is a halogen atom selected from iodine; and
optionally, wherein the reductive dehalogenation reaction is conducted in an alcohol selected from ethanol, methanol, isopropanol and a mixture thereof.

The Urushibara metal catalyst in said embodiments is preferably a catalyst prepared from iron or copper. Preferably the catalyst used in the method is an Urushibara iron catalyst (e.g. U—Fe—B), obtainable by combining elemental iron in powdered form with an excess of zinc (in powdered or grained form) and digesting or washing the resulting combination with a basic reagent, e.g. a solution of sodium hydroxide.

In another embodiment, the method according to the invention for preparing a semifluorinated alkane compound represented by the formula (1)

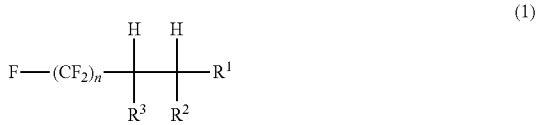

comprises the steps of
a) providing a compound of the formula (2);

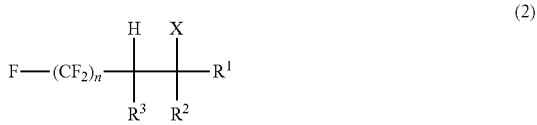

and
b) subjecting said compound of Formula (2) to a reductive dehalogenation reaction in the presence of an Urushibara metal catalyst, and a reducing agent,
wherein in formula (1) and (2)
n is an integer from 2 to 12;
$R^1$, $R^2$ and $R^3$ are the same or different and are independently from each other one selected from hydrogen and a $C_{1-10}$ linear or branched alkyl group; and
X is a halogen atom selected from chlorine, bromine and iodine.

Preferably, the method of the present invention step b) may comprise of the following steps: (i) providing a compound of Formula (2) in a solvent; (ii) addition of the Urushibara catalyst; (iii) addition of a reducing agent.

More preferably, step b) may comprise of the following steps: (i) providing a compound of Formula (2) in a solvent, preferably a linear or branched $C_{1-10}$ alcohol with a boiling point between 60° C. to 85° C.; (ii) adding a Urushibara metal catalyst, preferably in an amount of 6 wt % to 14 wt %, based on the amount of a compound of Formula (2); (iii) adding a reducing agent, wherein the reducing agent is a compound of Formula (3) MBHxZy, wherein M represents an alkali metal atom such as lithium, sodium or potassium, and Z represents a hydrogen atom, a cyano group, an alkoxy group or an acyloxy group, and x is an integer of 1 to 4 and y is an integer of 0 to 3, and the sum of x and y is 4, wherein the reducing agent is preferably added in an amount of 2 to 6 molar equivalents relative to that of compound of Formula (2).

Preferably, the dehalogenation reduction reaction is conducted under reflux conditions, preferably for about 3 to 5 hours. Optionally, in step (iii) of above embodiments, the addition of the reducing agent may be conducted under cooling conditions, so as to keep the temperature constant during addition of the reducing agent.

Even more preferably, step b) of the method according to the invention may comprise of the following steps: (i) providing a compound of Formula (2) in a solvent selected from methanol, ethanol and isopropanol; (ii) adding a Urushibara metal catalyst in an amount of 6 wt % to 14 wt %, based on the amount of a compound of Formula (2); (iii) adding a reducing agent, wherein the reducing agent is sodium borohydride, preferably in an amount of between 2 to 6 molar equivalents, or more preferably, 4 molar equivalents relative to the amount of compound of Formula (2). Preferably, the dehalogenation reduction reaction is conducted under reflux conditions. In said embodiment, the total reaction time is preferably about 3 to 5 hours. Step (iii) may also be conducted under cooling conditions, i.e. so as to keep the temperature constant during addition of the reducing agent.

The Urushibara metal catalyst featured in said method embodiments may be any one of the embodiments of the catalyst as described above, likewise the compounds of Formula (1) or (2) may be in accordance with any one of the previously described preferred embodiments.

Preferably, the Urushibara metal catalyst is a catalyst prepared from iron, for instance a catalyst as defined by the general formula U—Fe—B. In particular, such catalyst preferably is obtainable by combining elemental iron in powdered form with an excess of zinc in powdered or grained form and digesting or washing the resulting combination with a basic reagent, e.g. a solution of sodium hydroxide In another specific and preferred embodiment, the method of the present invention may relate to a method of preparing a compound of formula $C_nF_{2n+1}C_mH_{2m+1}$, preferably $F(CF_2)_n(CH_2)_mH$, wherein n and m are independently selected from an integer in the range of 2 to 12; wherein step (b) of the method may comprise of the following steps: (i) providing a compound of formula $C_nF_{2n+1}CH_2CHXC_{m-2}H_{2m-3}$, preferably $F(CF_2)_nCH_2(CHX)(CH_2)_{m-2}H$, wherein X is a halogen, preferably an iodine, and wherein n and m are independently selected from an integer in the range of 2 to 12, in an alcohol selected from methanol, isopropanol and ethanol; (ii) adding a Urushibara metal catalyst in an amount of 6 wt % to 14 wt % based on the amount of the compound of step (i); (iii) adding a reducing agent wherein the reducing agent is sodium borohydride, preferably added in an amount of between 2 to 6 molar equivalents, or more preferably, 4 molar equivalents.

Preferably, said dehalogenation reduction reaction may be conducted under reflux conditions. Optionally, step (iii) may also be conducted under cooling conditions, i.e. so as to keep the temperature constant during addition of the reducing agent. In said embodiment, the total reaction time is preferably between 3 to 5 hours. The Urushibara metal catalyst may be a catalyst such as defined in any of the above described embodiments, although preferably, the Urushibara metal catalyst is a catalyst prepared from iron, for instance a catalyst as defined by the general formula U—Fe—B. Such catalyst may be obtainable by combining elemental iron in powdered form with an excess of zinc in powdered or grained form and digesting or washing the resulting combination with a basic reagent, e.g. a solution of sodium hydroxide.

In chemistry, yield, also referred to as reaction yield, is the amount of product obtained in a chemical reaction. The absolute yield can be given as the weight in grams or in moles (molar yield). The percentage yield (or fractional yield or relative yield), which serves to measure the effectiveness of a synthetic procedure, is calculated by dividing the amount of the obtained desired product by the theoretical yield (the unit of measure for both must be the same).

The theoretical yield is the amount predicted by a stoichiometric calculation based on the number of moles of all reactants present. This calculation assumes that only one reaction occurs and that the limiting reactant reacts completely.

As used herein, the term conversion refers to how much reactant was used up as a fraction or percentage of the theoretical amount.

As used herein, the term purity refers to the purity, in the form of the fraction of product compared to other compounds, as measured by gas chromatography/mass spectroscopy analysis.

As used herein, the term crude yield refers to the yield of the product obtained in the dehalogenation reaction prior to purification.

As used herein, the term step yield refers to the yield of the semifluorinated product obtained in the dehalogenation reaction after purification of the crude product.

As used herein, the term overall yield refers to the amount of the semifluorinated product obtained at the end of the two step reactions, i.e. the addition reaction of an F-alkyl halides to a multiple bond, followed by reductive dehalogenation of the resulting halogenated adduct.

The meaning of the abbreviations in the following examples is as follows: h means hour(s), mL means milliliter(s), g means gram, mg means milligram(s), mmol means millimole, equiv. means molar equivalent, n means mole(s), NMR denotes nuclear magnetic resonance, GC/MS gas chromatography/mass spectrometry.

EXAMPLES

Next, the present invention will be described in the following examples. However, the present invention is not intended to be limited thereto.

All $^1$H-NMR analysis was carried out at 300 MHz.

GC/MS conditions: instrument GC Agilent 7890 A; column Agilent 122-5062 DB-5 60 m×250 m×0.25 m type; pressure 12.836 psi; flow 0.8 ml/min; reagent n-pentane ≥99%

Example 1: Preparation of Basic Urushibara Catalyst with Iron (U—Fe—B)

3 g Fe powder and 27 g Zn powder were mixed and transferred into a 500 ml flask. After addition of 330 g of 10% sodium hydroxide solution, the mixture was heated up to 50-55° C. for 15 minutes with occasional stirring. The supernatant liquor was decanted and the residue was washed with two 100 ml portions of hot water and then with two 50 ml portions of ethanol. 28.76 g of the catalyst was obtained. The catalyst was stored in ethanol until use.

Example 2: Preparation of an Iodinated Adduct

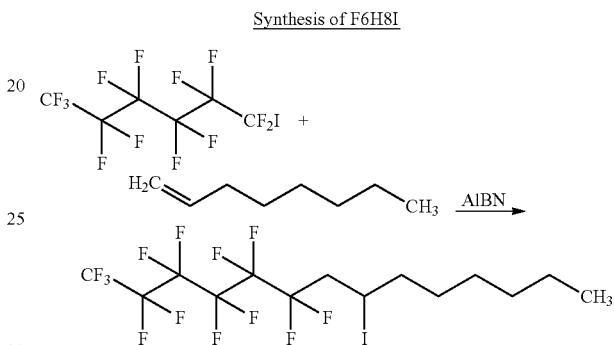

Synthesis of F6H8I

| Compound | g/mol | g | mol | mL | Equivalents |
|---|---|---|---|---|---|
| F61 | 445.95 | 891.90 | 2 | 433.0 | 1 |
| 1-Octene | 112.21 | 224.42 | 2 | 316.1 | 1 |
| AIBN | 164.21 | 7.88 | 0.048 | | 0.024 |
| F6H8I | 558.16 | 1116.32 | 2 | 150 | |

F61 (perfluorohexyl iodide), 1-octene and AIBN were added to a pressure reactor and heated up to 100° C. The mixture was stirred at 100° C. for three days. Afterwards, 20 g MgSO$_4$ and 2 g activated charcoal were added after cooling at room temperature. The mixture was filtered to give a yellow oily liquid.

The amount of crude product obtained was 1006.31 g (90% crude yield). After purification 704.81 g of F6H8I were collected (63% pure yield).

$^1$H NMR (CDCl$_3$): δ=0.89 (t, J=6.09 Hz, 3H), 1.2-1.51 (m, 8H), 1.87-1.71 (m, 2H), 3.04-2.66 (m, 2H), 4.41-4.21 (m, 1H)

Example 3: Synthesis of F6H8

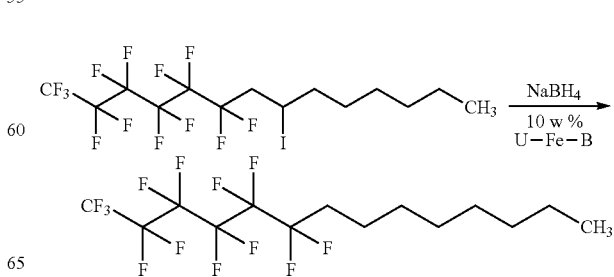

| Compound | g/mol | g | mol | mL | Equivalents |
|---|---|---|---|---|---|
| F6H8I | 558.16 | 27.91 | 0.050 | | 1.00 |
| 10 wt% U—Fe—B | | 2.79 | | | |
| NaBH$_4$ | 37.83 | 7.57 | 0.200 | | 4.00 |
| EtOH | | | | 150 | |

In a 500-ml three-neck flask equipped with a magnetic stirrer and a reflux condenser, 0.05 moles (27.91 g, 1 eq.) of F6H8I, produced as described in Example 2, were dissolved in ethanol (150 ml). To the solution/mixture 10 wt % of the catalyst U—Fe—B, prepared according to Example 1, was added. Further, 7.57 g (4 eq.) of NaBH$_4$ were slowly added by cooling the flask with ice. The mixture was stirred until no H$_2$ was produced. The surface of the mixture became gelatinous. Afterwards, the mixture was heated up to reflux for 4 hours. After cooling at room temperature, 50 ml of conc. HCl (1M) were added. The mixture became very viscous. About 200 ml water were added until the suspended solid was dissolved. The solution became green and changed rapidly to yellow.

The mixture was filtered into a separatory funnel. The below SFA was collected. The water phase was extracted once with n-pentane and combined with the SFA phase. It was finally washed once with a saturated Na$_2$S$_2$O$_3$ solution and dried with MgSO$_4$. N-pentane was removed in vacuum at 0.70 mbar.

Step yield: 92.70 g (72%)

$^1$H NMR (CDCl$_3$): δ=0.89 (t, =6.4 Hz, 3H), 1.22-1.44 (m, 10H), 1.52-1.65 (m, 2H), 1.93-2.14 (m, 2H).

GC/MS of the crude product: R$_t$=20.314; m/z=403.1 & 432.1 (purity: 99.226%). See also FIG. 1.

Example 4: Synthesis of F4H5

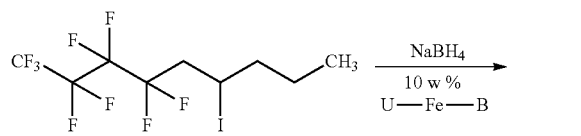

| Compound | g/mol | g | mol | mL | Equivalent |
|---|---|---|---|---|---|
| F4H5I | 416.07 | 55.80 | 0.134 | | 1.00 |
| 10 wt% U—Fe—B | | 5.58 | | | |
| NaBH$_4$ | 37.83 | 20.29 | 0.536 | | 4.00 |
| EtOH | | | | 300 | |

In a 1 L three neck flask equipped with a mechanical stirrer and a reflux condenser, 0.1 moles (55.80 g, 1 eq.) of F4H5I, produced analogously in accordance with the method of Example 2, were dissolved in ethanol (300 ml). To the solution/mixture 10 wt % of the catalyst U—Fe—B, prepared according to Example 1, was added. Further, 4 eq. (20.29 g) of NaBH$_4$ were slowly added. The mixture was stirred until no H$_2$ was produced (the surface of the mixture became gelatinous). After this, the mixture was heated up to reflux for 4 hours.

After cooling at room temperature, conc. HCl (50 ml) was added and the mixture became very viscous. About 200 mL water were added until the suspended solid was dissolved. The solution became green and changed rapidly to yellow.

The mixture was poured into a separatory funnel. The below SFA was collected, washed once with saturated Na$_2$S$_2$O$_3$ solution and dried with MgSO$_4$. The product was not dried in vacuum, because it evaporated very fast.

Step yield: 30%

$^1$H NMR (CDCl$_3$): δ=0.92 (t, J=6.09 Hz, 3H), 1.28-1.44 (m, 4H), 1.56-1.68 (m, 2H), 1.94-2.14 (m, 2H)

Figure 2:
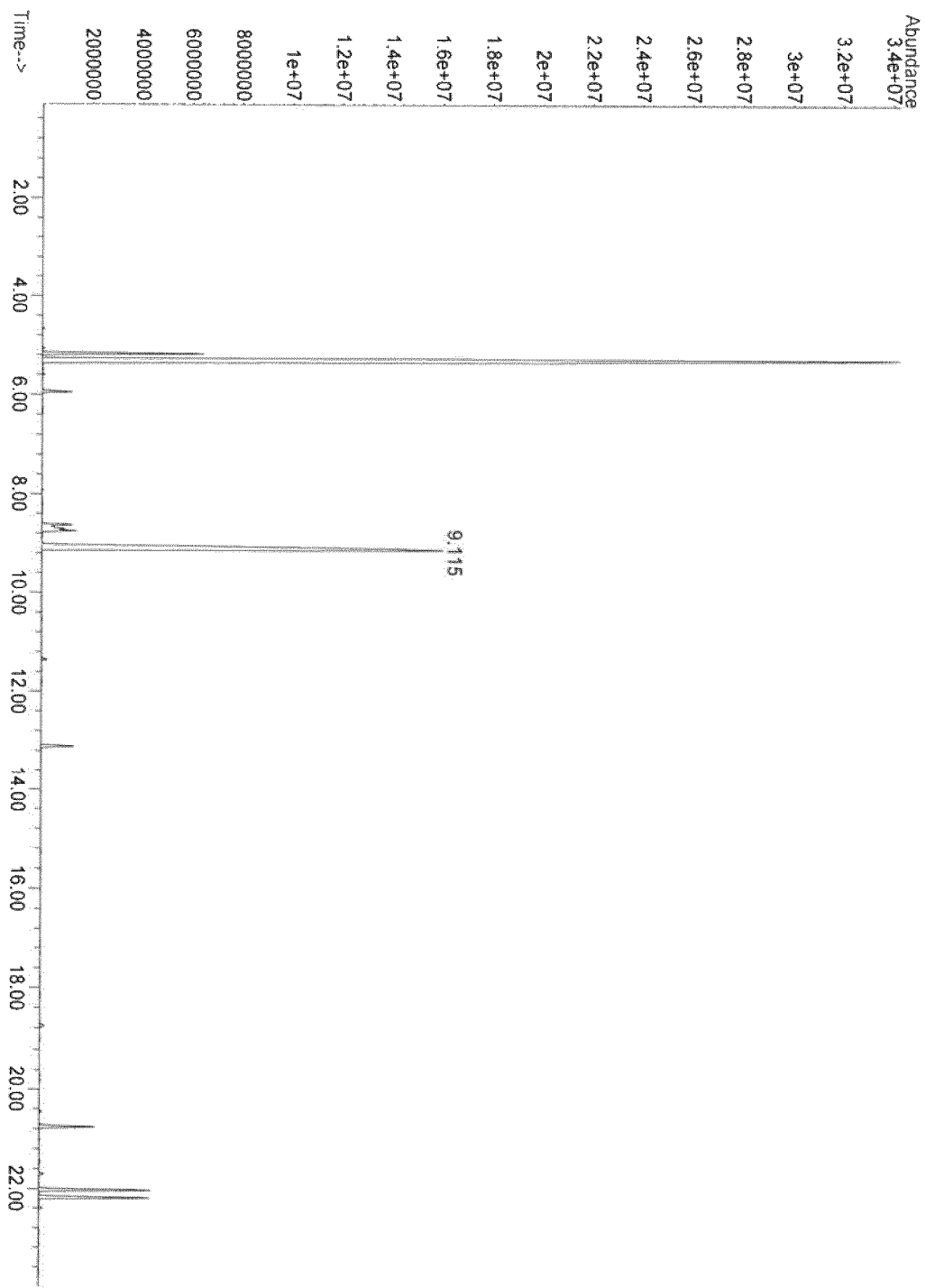
FIG. 2: GC/MS spectrum of F4H5
Figure 3:
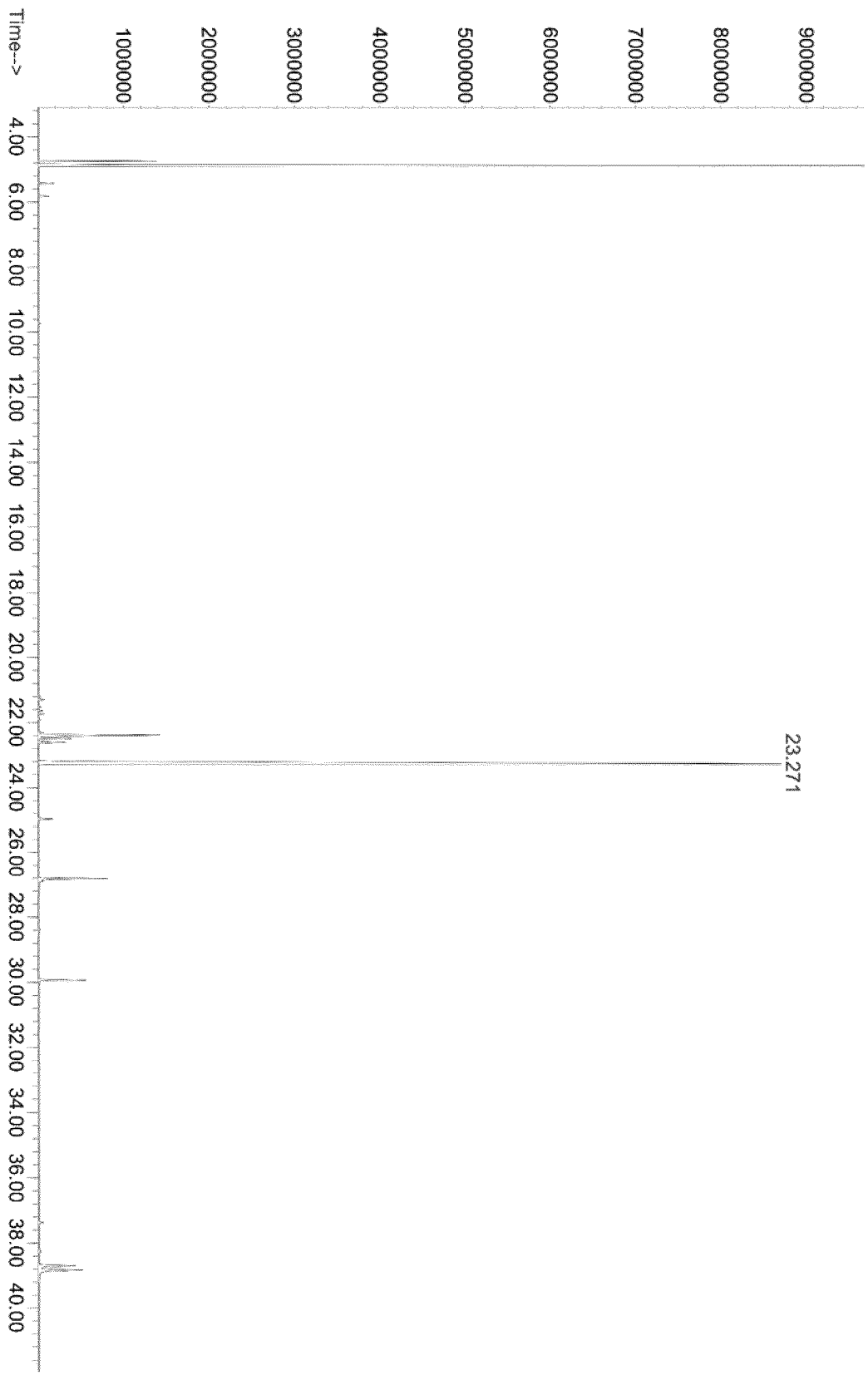
FIG. 3: GC/MS spectrum of F8H8

GC/MS of the crude product: Rt=9.115; m/z=121.0+ 195.0. (purity: 63.661%). See FIG. 2.

Example 5: Synthesis of F8H8

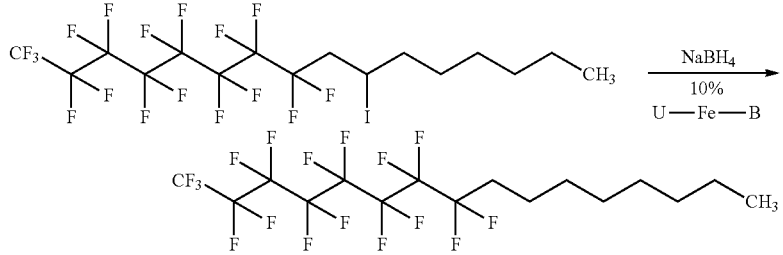

| Compound | g/mol | g | mol | mL | equivalent |
|---|---|---|---|---|---|
| F8H8I | 658.18 | 55.82 | 0.085 | | 1.00 |
| 10 wt% U—Fe—B | | 5.58 | | | |
| NaBH$_4$ | 37.83 | 12.86 | 0.340 | | 4.00 |
| EtOH | | | | 250 | |

In a 1 L three neck flask equipped with a mechanical stirrer and a reflux condenser, 0.085 moles of F8H8I, prepared analogously in accordance with the general method of Example 2, were dissolved in ethanol (250 ml). To the solution/mixture 10 wt % of the catalyst U—Fe—B, prepared according to Example 1, was added. Further, 4 equivalents of NaBH$_4$ were slowly added. The mixture was stirred until no H$_2$ was produced. The surface of the mixture became gelatinous. After this, the mixture was heated up to reflux for 4 hours.

After cooling at room temperature, conc. HCl (50 ml) was added. The mixture became very viscous. About 200 mL water was added until the suspended solid was dissolved. The solution became green and changed rapidly to yellow.

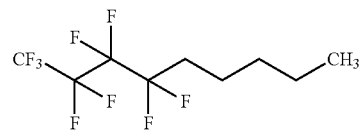

The mixture was poured into a separatory funnel. The below SFA was collected, washed once with saturated Na₂S₂O₃ solution and dried with MgSO₄. Ethanol from the reaction was removed in vacuum at 0.70 mbar. The product crystallised as fine light pink needles at 25° C.

Step yield: 53%

$^1$H NMR (CDCl₃): δ=0.89 (t, J=6.4 Hz, 3H), 1.28-1.41 (m, 10H), 1.51-1.66 (m, 2H), 1.93-2.14 (m, 2H)

GC/MS of the crude product: Rt=23.271; m/z=503.1+ 532.2. (purity: 70.925%)

Example 6: Synthesis of F6H8 with Different Urushibara Metal Catalysts

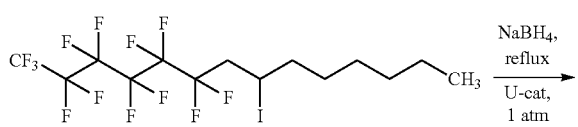

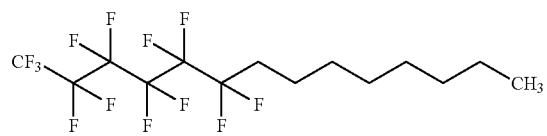

The same general procedure as described in Example 3 was conducted in the following Examples to synthesize F6H8 (Table 1). The reactions were carried out starting from 50 mmol of F6H8I which was prepared in accordance with Example 2. The Urushibara metal catalyst which were used were prepared analogously with the general method of Example 1.

TABLE 1

| Example | Cat. (wt %) | Pressure (Bar) | Time (h) | Temp. (° C.) | Concentration (M) | Solvent | Purity (%) | Crude yield (%) |
|---|---|---|---|---|---|---|---|---|
| 84 | 10% U—Fe—B | atm. | 4 | reflux | 1 | EtOH | 99 | 88 |
| 85 | 10% U—Fe—B | atm. | 2 | reflux | 1 | EtOH | 73 | 74 |

In the examples in Table 2 below, the Urushibara metal catalysts used in the reactions were prepared with Zn and treated with 10% NaOH in analogy to the method described in Example 1 for preparing the Fe catalyst (using Ni, Co, or Cu powder in case of the U—Ni—B, U—Co—B and U—Cu—B catalysts). The reductive dehalogenation reactions were carried out starting from 0.1 mol of the iodinated adduct F6H8I, prepared according to Example 2, under reflux for 4 hours at 1013 mbar.

TABLE 2

| Ex. | Catalyst 10 wt % | NaBH₄ (eq.) | Solvent | Purity (%) (GC/MS) | Conversion (%) | Crude yield (%) | Step yield (%) |
|---|---|---|---|---|---|---|---|
| 98 | U—Ni—B | 4 | EtOH | 68 | 99 | 54 | 36 |
| 99 | U—Co—B | 4 | EtOH | 50 | 99 | 49 | 24 |
| 101 | U—Cu—B | 4 | EtOH | 74 | 99 | 60 | 44 |
| 109 | U—Fe—B | 4 | EtOH | 62 | 99 | 83 | 51 |
| 122 | U—Fe—B | 4 | MeOH | 50 | 77 | — | 35 |
| 127 | U—Cu—B | 4 | MeOH | 57 | 79 | — | 57 |
| 123 | U—Fe—B | 4 | i-PrOH | 55 | 87 | — | 35 |
| 124 | U—Cu—B | 4 | i-PrOH | 51 | 81 | — | 41 |

The Urushibara metal catalysts used in the examples of Table 3 are also prepared with Zn but treated with 13% HOAc. The reduction reactions were performed with 0.1 mol of the iodinated adduct, under reflux for 4 hours, at 1013 mbar and using 10 wt % of the Urushibara catalyst.

TABLE 3

| Ex. | Catalyst 10 wt % | NaBH₄ (eq.) | Solvent | Conversion (%) | Purity (%) (GC/MS) | Step yield (%) |
|---|---|---|---|---|---|---|
| 120 | U—Fe—A | 4 | EtOH | 82 | 55 | 40 |
| 121 | U—Cu—A | 4 | EtOH | 86 | 59 | 45 |
| 130 | U—Fe—A | 4 | MeOH | 79 | 59 | 43 |
| 131 | U—Cu—A | 4 | MeOH | 80 | 54 | 40 |

In the Examples featured in Table 4, the Urushibara metal catalyst is U—Fe—B prepared with Zn and activated with 10% NaOH, in accordance with the general method described in Example 1. The reductive dehalogenation reactions are carried out in methanol, and using 4 equivalents of the reducing agent relative to the amount of the starting material F6H8I

TABLE 4

| Ex. | Catalyst 10 wt % | Reducing Agent | Purity (%) (GC/MS) | Crude yield (%) | Step yield (%) | Conversion (%) |
|---|---|---|---|---|---|---|
| 133 | U—Fe—B | NaBH₄ | 80 | 69 | 55 | 99 |
| 138 | U—Fe—B | LiBH₄ | 56 | 71 | 40 | 78 |
| 139 | U—Fe—B | NaBH(OAc)₃ | 51 | 55 | 28 | 79 |
| 141 | U—Fe—B | NaBH₃CN | 58 | 61 | 32 | 90 |

Comparative Example 1

Synthesis of F6H8 with $H_2$ and Pd/C.

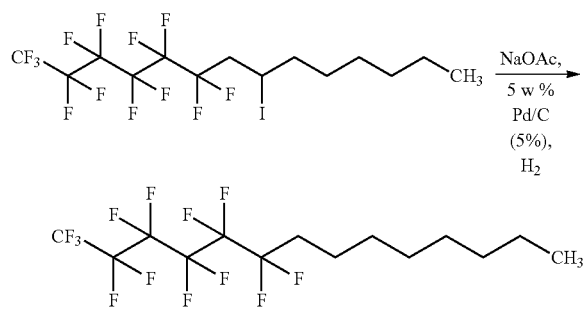

0.2 mol of F6H8I was added to a pressure reactor and mixed with 200 ml EtOH, 0.40 mol NaOAc and 5 wt % Pd/C (5%). The reactor was loaded with 5 bar $H_2$ and heated up to 40° C. The temperature increased and reached about 80° C. The mixture was stirred for 24 hours and 40° C. After cooling at room temperature, 100 ml water and 20 ml HCl were added. The SFAs phase was collected and washed with $Na_2S_2O_3$, dried with $MgSO_4$ and dried in vacuum.

GC/MS of the crude reaction product:
Rt=19.269 (21.319%) alkene
Rt=20.265 (33.711%) F6H8
Rt=27.326 (0.117%) F6H8I
Step Yield: ~34%

In contrast to the method of Example 3 of the invention, it is observed that the dehalogenation of F6H8I based on hydrogen and Pd/C requires longer reaction time and yet provides poor and lower conversion to the desired dehalogenated product, as well as formation of undesired side product such as the alkene as observed by GC-MS analysis of the crude reaction product.

Further dehalogenation reactions based on Pd/C or Pd/Al and hydrogen were conducted under analogously, at 10 bar pressure of $H_2$, and at a concentration of 1M. The results are summarized in Table 5 below.

TABLE 5

| Catalyst (wt %); reagent | Base (eq.) | $H_2$ (Bar) | Time (hours) | Temp. (° C.) | Solvent | Purity (%) (GC/MS) | Crude yield (%) |
|---|---|---|---|---|---|---|---|
| 5% Pd/C; 50 mmol | NaOAc (2.0) | 10 | 24 | 40 | iPrOH | 93 | 39 |
| 5% Pd/C; 50 mmol | NaOAc (2.0) | 10 | 23 | 40 | EtOH | 91 | 36 |
| 5% Pd/Al; 50 mmol | NaOAc (2.0) | 10 | 25 | 40 | iPrOH | Starting material | — |
| 5% Pd/C; 200 mmol | NaOAc (2.0) | 10 | 24 | 80 | iPrOH | 71 | 41 |
| 5% Pd/C; 200 mmol | NaOAc (2.0) | 10 | 23 | 80 | EtOH | 60 | 41 |
| 5% Pd/C; 200 mmol | NaOAc (2.0) | 10 | 24 | 80 | MeOH | 34 | 35 |
| 5% Pd/C; 200 mmol | Sat. $NaHCO_3$ (2.0) | 10 | 24 | 40 | EtOH | 38 | 36 |

TABLE 6

| Cat. (wt %); reagent | Base (eq.) | Reducing agent | Time (h) | Time/ Temp. (° C.) | Solvent | Purity (%) (GC/MS) | Crude yield (%) |
|---|---|---|---|---|---|---|---|
| 5% Pd/C; 50 mmol | — | $NaBH_4$ | 24 | 4 hours Reflux; r.t. over night | EtOH | 25 | 18 |
| 5% Pd/C; 50 mmol | NaOAc (2.0) | $NaBH_4$ | 23 | 4 hours Reflux; r.t. over night | EtOH | 28 | 30 |

TABLE 6-continued

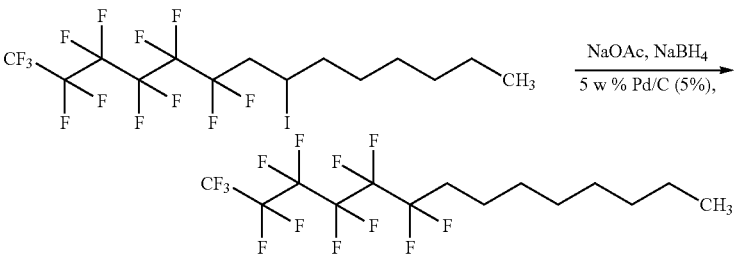

| Cat. (wt %); reagent | Base (eq.) | Reducing agent | Time (h) | Time/ Temp. (° C.) | Solvent | Purity (%) (GC/MS) | Crude yield (%) |
|---|---|---|---|---|---|---|---|
| 5% Pd/C; 50 mmol | NaOAc (2.0) | NaBH$_4$* | 25 | 4 hours Reflux; r.t. over night | EtOH | 13 | — |
| 5% Pd/C; 50 mmol | NaOAc (2.0) | NaBH$_4$* | 25 | 4 hours reflux, r.t. over night | DEGEE | Only alkene | — |
| 5% Pd/C; 50 mmol | NaOAc (2.0) | NaBH$_4$ |  | Reflux over night | EtOH | 24 | 23 |
| 5% Pd/C; 50 mmol | NaOAc (2.0) | NaBH$_4$* |  | Reflux over night | EtOH | 34 | 19 |
| 10% Raney-Ni; 50 mmol | — | NaBH$_4$ | 24 | Reflux over night | EtOH | Starting material (F6H8I) | — |

*as a 12% solution in water

INDUSTRIAL APPLICABILITY

By using the method of production of the present invention, the reaction time of the reductive dehalogenation reaction can be significantly shortened as compared to reaction time in previous methods. In particular, even in case of using an apparatus for industrial production, the reaction offers a more simplified process, and can be completed in a shorter time and with inexpensive reagents.

The invention claimed is:

1. A method for producing a semifluorinated alkane of the formula (1)

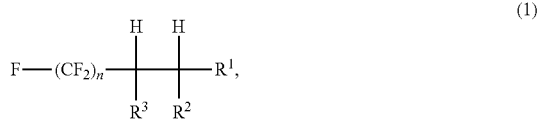

wherein the method comprises the step of subjecting a compound of the formula (2)

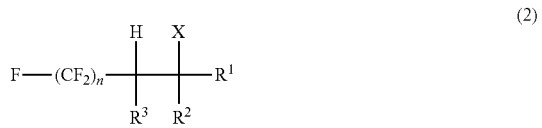

to a reductive dehalogenation reaction in the presence of a Urushibara metal catalyst and a reducing agent,
wherein in the formulas (1) and (2):
n is an integer from 2 to 12;
$R^1$, $R^2$ and $R^3$ are the same or different and are independently selected from hydrogen and a $C_{1-10}$ linear or $C_{1-10}$ branched alkyl group; and
X is a halogen atom selected from chlorine, bromine and iodine.

2. The method according to claim 1, wherein $R^1$ is selected from hydrogen and a $C_{1-10}$ linear or $C_{1-10}$ branched alkyl group; and $R^2$ and $R^3$ are independently selected from hydrogen and a $C_{1-10}$ linear alkyl group.

3. The method according to claim 2, wherein $R^1$ is selected from hydrogen and a $C_{1-10}$ linear or $C_{1-10}$ branched alkyl group; and $R^2$ and $R^3$ are independently selected from hydrogen and a $C_{1-6}$ linear alkyl group.

4. The method according to claim 3, wherein $R^1$ is selected from hydrogen and a $C_{1-10}$ linear or $C_{1-10}$ branched alkyl group; $R^2$ is selected from hydrogen and a $C_{1-6}$ linear alkyl group; and $R^3$ is selected from hydrogen and methyl.

5. The method according to claim 4, wherein $R^1$ is selected from hydrogen and a $C_{1-6}$ linear or $C_{1-6}$ branched alkyl group; and $R^2$ and $R^3$ are independently selected from hydrogen and a methyl group.

6. The method according to claim 5, wherein $R^1$, $R^2$ and $R^3$ are hydrogen; or
wherein $R^1$ and $R^2$ are hydrogen, and $R^3$ is methyl; or
wherein $R^1$ is methyl, $R^2$ is hydrogen and $R^3$ is methyl; or
wherein $R^1$ and $R^2$ are methyl, and $R^3$ is hydrogen; or
wherein $R^1$ is ethyl, $R^2$ is methyl, and $R^3$ is hydrogen; or
wherein $R^1$ is isopropyl, and $R^2$ and $R^3$ are hydrogen; or
wherein $R^1$ is a $C_{1-6}$ linear alkyl group, and $R^2$ and $R^3$ are hydrogen.

7. The method according to claim 5, wherein $R^1$ is selected from hydrogen and a $C_{1-6}$ linear alkyl group; and $R^2$ and $R^3$ are hydrogen.

8. The method according to claim 1, wherein n is an integer selected from 4 to 8.

9. The method according to claim 1, wherein the Urushibara metal catalyst is prepared by using a metal selected from iron, copper, nickel or cobalt.

10. The method according to claim 1, wherein the amount of Urushibara catalyst is from 8 to 12 weight percent (wt %) based on the amount of the compound of formula (2).

11. The method according to claim 1, wherein the reducing agent is selected from a complex compound of a borohydride or a complex compound of aluminium hydride.

12. The method according to claim 11, wherein the reducing agent is selected from sodium borohydride, lithium borohydride, potassium borohydride, calcium borohydride, zinc borohydride, sodium triacetoxy borohydride, sodium cyanoborohydride and lithium aluminium hydride, and mixtures thereof.

13. The method according to claim 12, wherein the reducing agent is sodium borohydride.

14. The method according to claim 1, wherein the amount of the reducing agent is from 2 to 6 equivalents with respect to the compound of formula (2).

15. The method according to claim 1, wherein the reductive dehalogenation is carried out by using as a solvent an alcohol selected from ethanol, methanol and iso-propanol.

16. The method according to claim 1, wherein the halogen atom X is iodine.

17. The method according to claim 16, wherein in formulas (1) and (2), n is an integer from 4 to 8; $R^1$ is selected from ethyl, n-propyl, n-butyl, n-pentyl and n-hexyl, and $R^2$ and $R^3$ are both hydrogen.

18. The method according to claim 17, wherein the Urushibara metal catalyst is a catalyst prepared from iron or copper.

19. The method according to claim 18, wherein the amount of Urushibara catalyst is from 8 to 12 weight percent (wt %) based on the amount of the compound of formula (2).

20. The method according to claim 19, wherein the reducing agent is sodium borohydride.

21. The method according to claim 1, wherein:
in formulas (1) and (2) n is 6, $R^1$ is n-hexyl, and $R^2$ and $R^3$ are both hydrogen; or
in formulas (1) and (2) n is 4, $R^1$ is n-propyl, and $R^2$ and $R^3$ are both hydrogen; or
in formulas (1) and (2) n is 6, $R^1$ is n-pentyl, $R^2$ is hydrogen, and $R^3$ is methyl; or
in formulas (1) and (2) n is 4, $R^1$ is ethyl, $R^2$ is hydrogen, and $R^3$ is methyl.

22. The method according to claim 21, wherein in formulas (1) and (2) n is 6, $R^1$ is n-hexyl, and $R^2$ and $R^3$ are both hydrogen.

23. The method according to claim 21, wherein in formulas (1) and (2) n is 4, $R^1$ is n-propyl, and $R^2$ and $R^3$ are both hydrogen.

24. The method according to claim 16, wherein:
in formulas (1) and (2) n is 6, $R^1$ is n-hexyl, and $R^2$ and $R^3$ are both hydrogen; or
in formulas (1) and (2) n is 4, $R^1$ is n-propyl, and $R^2$ and $R^3$ are both hydrogen; or
in formulas (1) and (2) n is 6, $R^1$ is n-pentyl, $R^2$ is hydrogen, and $R^3$ is methyl; or
in formulas (1) and (2) n is 4, $R^1$ is ethyl, $R^2$ is hydrogen, and $R^3$ is methyl.

25. The method according to claim 21, wherein:
in formulas (1) and (2) n is 6, $R^1$ is n-pentyl, $R^2$ is hydrogen, and $R^3$ is methyl; or
in formulas (1) and (2) n is 4, $R^1$ is ethyl, $R^2$ is hydrogen, and $R^3$ is methyl.

26. The method according to claim 24, wherein:
in formulas (1) and (2) n is 6, $R^1$ is n-pentyl, $R^2$ is hydrogen, and $R^3$ is methyl; or
in formulas (1) and (2) n is 4, $R^1$ is ethyl, $R^2$ is hydrogen, and $R^3$ is methyl.

\* \* \* \* \*